United States Patent
Wang et al.

(10) Patent No.: US 8,508,234 B2
(45) Date of Patent: Aug. 13, 2013

(54) METHOD AND DEVICE FOR DETECTING FAILURES IN INDUCTIVE CONDUCTIVITY MEASUREMENTS OF A FLUID MEDIUM

(75) Inventors: Changlin Wang, Shanghai (CN); Fengjin Wang, Shanghai (CN); Jun Xia, Shanghai (CN); Xiaokai Wang, Shanghaus (CN); Jürgen Ammann, Zürich (CH)

(73) Assignee: Mettler-Toledo AG, Greifensee (CH)

( * ) Notice: Subject to any disclaimer, the term of this patent is extended or adjusted under 35 U.S.C. 154(b) by 317 days.

(21) Appl. No.: 13/006,045

(22) Filed: Jan. 13, 2011

(65) Prior Publication Data

US 2011/0163756 A1 Jul. 7, 2011

Related U.S. Application Data

(63) Continuation of application No. PCT/EP2009/005073, filed on Jul. 13, 2009.

(30) Foreign Application Priority Data

Jul. 14, 2008 (CN) .......................... 2008 1 0040544

(51) Int. Cl.
*G01R 31/02* (2006.01)
*G01N 27/02* (2006.01)

(52) U.S. Cl.
USPC .............................. 324/537; 324/445

(58) Field of Classification Search
USPC ............................. 324/439–446, 537
See application file for complete search history.

(56) References Cited

U.S. PATENT DOCUMENTS

| | | | |
|---|---|---|---|
| 2,542,057 A | 2/1951 | Relis | |
| 4,220,920 A * | 9/1980 | Gross | ............... 324/442 |
| 5,341,102 A | 8/1994 | Akiyama et al. | |
| 5,455,513 A | 10/1995 | Brown et al. | |
| 6,414,493 B1 | 7/2002 | Rezvani | |
| 2003/0197499 A1 | 10/2003 | Wieland et al. | |

* cited by examiner

*Primary Examiner* — Vincent Q Nguyen
(74) *Attorney, Agent, or Firm* — Standley Law Group LLP

(57) ABSTRACT

Exemplary embodiments of the present invention are directed to methods and devices for detecting open-circuit and short-circuit failure in an electromagnetic (inductive) measurement of the conductivity of liquids and on the sensor and cable wiring. An electromagnetic measurement of the conductivity of a liquid is performed by immersing a sensor into the liquid, wherein the sensor includes at least 2 toroidal cores, one of them carrying an excitation coil and the other carrying an induction coil. When an AC excitation voltage is applied to the excitation coil, an induced current or voltage can be measured in the induction coil which is proportional to the conductivity of the measured liquid.

16 Claims, 1 Drawing Sheet

METHOD AND DEVICE FOR DETECTING FAILURES IN INDUCTIVE CONDUCTIVITY MEASUREMENTS OF A FLUID MEDIUM

CROSS-REFERENCE TO RELATED APPLICATIONS

This application is a continuation under 35 USC §120 of PCT/EP2009/005073, filed on 13 Jul. 2009 which is, in turn, entitled to, and claims, benefit of a right of priority under 35 USC §119 from Chinese Patent Application No. 200810040544.5, filed on 14 Jul. 2008. The content of each of these applications is incorporated by reference as if fully recited herein.

TECHNICAL FIELD

Exemplary embodiments of the present invention involve methods and circuits for detecting failures in a measuring device for electromagnetic or inductive measurements of the electrical conductivity of fluid medium, in particular a liquid or a solution and a corresponding measurement device.

Conductivity measurements of a fluid medium involve a measuring device, which typically comprises a measurement sensor, which is immersed into the fluid medium, a measurement circuit and a cable wiring, which connects the measurement sensor to the measurement circuit. Exemplary embodiments according to the invention concern methods and devices for detecting a failure/non-failure condition of this measurement device, in particular an open-circuit and/or a short-circuit failure in the measurement sensor, in a cable wiring or in the input circuit.

BACKGROUND

The conductivity of a liquid is an important analysis parameter of electrochemistry. Its measurement has wide application in fields like the chemical industry, metallurgy, biology, medicine, grain testing, water conservancy, energy resources, etc. Conductivity measuring methods can be divided into 2 groups: contact-type and non-contact type.

A non-contact type measurement applies the principle of electromagnetic induction and is therefore also referred to as an electromagnetic conductivity measuring method or an inductive conductivity measuring method. As there is no contact between the conductive part of the measuring component and the measured liquid, sensors of this type possess the advantages of good solidity, corrosion resistance, non-polarization and long service life. There has been a long history of development since the basic principle of electromagnetic measurement of the conductivity of a liquid was invented and applied in practice.

For example, U.S. Pat. No. 2,542,057 to M. J. Relis opened the basic theory to the public in 1951. The related sensor according to this reference employs a pair of coaxial toroidal cores which are covered by corrosion-protective and electrically insulating material. The inner hole of the 2 toroidal cores allows the current path through the liquid. According to the electromagnetic induction principle, when an alternating current is sent through the excitation coil, an alternating magnetic flux is generated in the excitation toroidal core, which in turn generates an induction current through the loop in the measured liquid. The induction current generated in the loop presents itself as a current loop which crosses both the excitation toroidal core and the pick-up toroidal core. This current loop generates an alternating magnetic flux in the toroidal core, which generates in the induction coil an induced current, which in turn produces an induced electrical voltage at the induction coil.

Because the induction current of the liquid is related to its conductivity, the induced current of the induction coil and the induced voltage (open-circuit voltage) is proportional to the current through the liquid. Thus, the conductivity of the liquid can be derived from the measurement of the induced current or the induced voltage. The conductivity G of the liquid is calculated from the formula $G=C/R$, wherein C is the sensor cell constant and R is the equivalent resistance of the loop through the liquid. As an alternative, the conductivity of the liquid can be computed from the current of the induction coil when the induced voltage at the terminal of the induction coil is zero as in the method introduced in U.S. Pat. No. 5,455,513 A1 to Neil L. Brown et al.

In the measurement of conductivity, it has also become more and more important to improve the reliability of the measuring process. If not investigated carefully, an open-circuit failure of the coils or the cable wiring could easily be mistaken for a conductivity of zero (or a very low conductivity), and thus an incorrect value may be inadvertently measured for the conductivity of the liquid.

U.S. Pat. No. 6,414,493 B1 to Behzad Rezvani discloses a method wherein an additional wire loop is introduced into the measurement sensor to form a conductive loop through the excitation coil and the induction coil. The excitation coil induces an alternating current into this wire loop, which in turn induces an additional alternating current in the induction coil to provide a base output signal. If an open circuit condition occurs in the coils, a corresponding change in the base output signal occurs, which can be detected. However, adding an additional loop to the toroidal cores makes the device more complicated.

SUMMARY OF THE INVENTIVE CONCEPT

Exemplary embodiments in accordance with the present invention therefore have the objective to overcome the drawbacks of the prior art, in particular to provide a simpler method, a simpler detection circuit and a corresponding measuring device to detect failures in inductive conductivity measurements in order to avoid the risk of inadvertently measuring an incorrect value for the conductivity.

The technical solution is provided by an exemplary detection method and an exemplary detection circuit, which comprise the features described in the independent claims. Further exemplary embodiments of the invention are disclosed in the additional dependent claims.

Exemplary embodiments according to the present invention disclose a method for detecting open-circuit and short-circuit failures of a measurement device for inductively measuring the electrical conductivity of a fluid medium with a sensor immersed in the fluid medium, which sensor comprises at least at least 2 toroidal cores, one of which carries an excitation coil and the other carries an induction coil. The measuring device includes an excitation driving circuit to supply the excitation coil inside the sensor with an excitation signal so that a current or voltage which is related to the conductivity of the measured liquid is induced in the induction coil, said method comprising the following steps: supplying a very small DC current to the terminals of the excitation coil or induction coil in order to monitor the DC voltage generated on the coils so that open-circuit failure of the device can be detected, and monitoring the output swing of the excitation driving circuit in order to detect a short-circuit failure of the device.

This results in a simple method and a simple and low-cost corresponding detection circuit, because there is no need to install further components in the measurement sensor. In particular a complicated and expensive installation of an additional loop in the coils is avoided. Therefore exemplary embodiments according to the present invention disclose a method and a device with a simple structural concept for detecting failures in electromagnetic (inductive) measurements of the conductivity of liquids.

In a first embodiment of the invention the additional applied signal is a current, in particular a direct current, commonly named as a DC signal.

In another embodiment of the invention the strength of the additional applied signal is very small and/or so small that it never brings the coil into saturation and/or that is less than several micro amperes and/or that is substantially less than the strength of the excitation current. This way the accuracy of the conductivity measurement is not affected.

In still another embodiment the derived signal is a voltage, in particular with strength of almost zero volt under regular operation conditions. Voltages can be measured in a direct manner and the zero voltage does not or only insignificantly affect the actual conductivity measurements.

In another exemplary embodiment the failure characteristics is an open-circuit failure or a short-circuit failure of the sensor or its at least one coil or of a connecting cable connected to the coil or of a measurement circuit connected to the coil.

In another embodiment the direct signal is delivered from a power source to the excitation coil via a resistor of high resistance.

In another exemplary embodiment the method comprises the additional steps: using the coil as an excitation coil for applying an alternating current to the fluid, measuring the swing of the excitation current to obtain a measurement value, comparing the measurement value to at least one further threshold value and depending upon the comparing step, triggering an action of the measurement device.

The swing characterizes the variability of the excitation current, typically the peak-to-peak amplitude. The presence of a short circuit failure is determined if the detected voltage swing deviates from the normal value. When short-circuit failure occurs at the excitation side, the output swing of excitation driving circuit will be lower than its normal value. This deviation can be detected directly or indirectly by means of an operational amplifier.

In another embodiment of the above method according to the invention, the step of supplying a very small DC current to the terminals of the excitation coil or induction coil includes delivering the small DC current to the coil terminals from a positive power source through a large value resistor. An open-circuit failure on the excitation coil or induction coil is present if the detected DC voltage exceeds a certain threshold voltage.

In other embodiments of the above exemplary method, the excitation driving circuit includes an operational amplifier and the step of detecting the output swing of the excitation driving circuit includes connecting the output of the operational amplifier and the output of the excitation driving circuit through a current-limiting resistor. The presence of a short circuit failure is determined if the detected voltage swing exceeds the normal value.

Exemplary embodiments of the present invention further involve a detection circuit for detecting a failure of a measurement device for inductively measuring the electrical conductivity of a fluid medium with a sensor, which comprises at least one coil, in particular an excitation coil or an induction coil, for applying to the fluid medium or receiving from the fluid medium an alternating current, said device comprises: a means for applying an additional excitation signal to the coil to generate a corresponding derived signal, which characterizes a failure/non-failure condition of the measurement device, and a measurement unit connectable to the coil and configured to measure the derived signal for obtaining a measurement value; a level detector, which is connected to the measurement unit for obtaining the measurement value, and is configured to compare the measurement value to at least one threshold value to obtain a comparing result, and comprises an output to trigger, depending upon the comparing result, an action of the measurement device.

Thereby the means for applying an excitation signal is a power source, which is connected, in particular via a high resistance resistor, to the at least one coil and which is operable to apply the additional excitation signal to the at least one coil.

In another embodiment the power source is operable to apply a substantially continuous signal, in particular a direct current (DC), to the coil.

In still another embodiment the output of the level detector is connectable to a display unit or a processing device to transmit the detection result for triggering the action of the measurement device.

Another embodiment of the present invention concerns a device for detecting open-circuit and short-circuit failure of electromagnetic (inductive) measurements of the conductivity of liquids. The device includes: an open-circuit detecting circuit, which operates by supplying a very small DC current to the terminals of the excitation coil or induction coil in order to detect the DC voltage generated on the coils so that open-circuit failure of the device can be detected; and a short-circuit detecting circuit for the excitation coil, which operates by monitoring the output swing of the excitation driving circuit in order to detect a short-circuit failure of the device.

In another embodiment of the exemplary detecting device, the open-circuit detecting circuit includes a DC power source which is connected to one terminal of the induction coil through a large value resistor, and a voltage level detector which is connected to the terminals of the excitation coil side and/or the induction coil side. If the detected DC level exceeds a threshold voltage, this is judged to be an indication that there is an open-circuit failure on the respective side.

The embodiments in accordance with the invention further involve a measurement device with an above detecting circuit and with an excitation driving circuit, which includes an operational amplifier whose positive input is connected to an excitation signal, a feedback resistor which connects the negative input of the operational amplifier and the output of the excitation driving circuit which is also connected to the excitation coil, and a current-limiting resistor which connects the excitation driving circuit and the excitation coil.

In other embodiments, the exemplary measurement device comprises a further detecting circuit for detecting a short-circuit failure of the excitation driving circuit, the further detecting circuit includes a pick-up circuit which is connected to the output of the operational amplifier, a peak-to-peak measuring circuit which is connected to the output of the pick-up circuit and generates a voltage that is available for detection and corresponds to the voltage swing of the operational amplifier; and a voltage level detector which is connected to said voltage that is available for detection. If the detected voltage level exceeds the threshold voltage, this is judged to be an indication that there is a short-circuit failure in the excitation coil.

Preferably the peak-to-peak measuring circuit includes a first diode which is connected in reverse orientation between the output of the pick-up circuit and the reference voltage, a second diode, which is connected in forward orientation between the output of the pick-up circuit and an output node which outputs the voltage for detection and, in particular a voltage-dividing circuit which is connected between the output node and the voltage level detector.

In another embodiment the exemplary measuring device comprises a inductive conductivity sensor, which is operably connected to the measurement unit, wherein the sensor is immersed into the fluid medium, in particular into a liquid or a solution, and/or wherein the coil of the sensor is carried by a toroidal core, in particular a ferrite ring or a magnetic ring.

Compared to the existing technology, the exemplary embodiments of the present invention introduce methods and devices for detecting open-circuit and short-circuit failure in electromagnetic (inductive) measurements of the conductivity of liquids with the following advantages: It uses a simple and low-cost circuit to detect an open-circuit failure or short-circuit failure of the measurement system in order to avoid the risk of inadvertently collecting erroneous measurement values for the conductivity, which makes the measurement result very reliable.

BRIEF DESCRIPTION OF THE DRAWINGS

In addition to the features mentioned above, other aspects of the invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
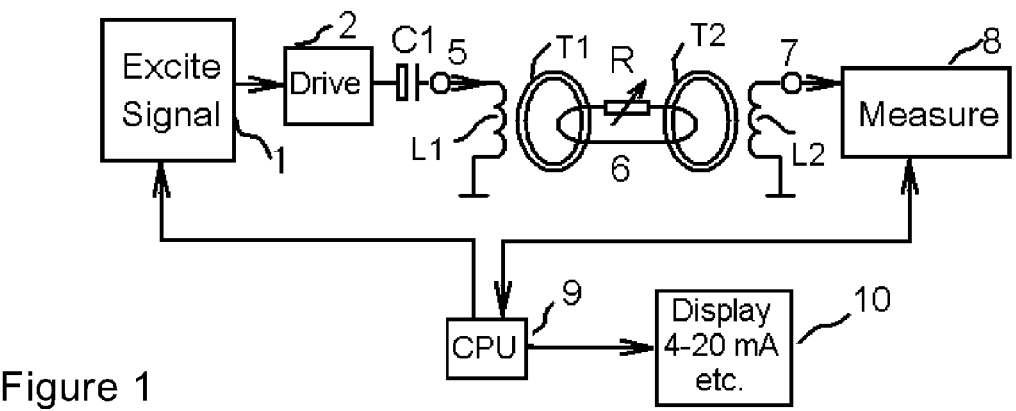
FIG. 1 is a schematic illustrating the principle of an exemplary method for inductive measuring of the conductivity of a liquid.

FIG. 1 schematically illustrates the principle of the device for electromagnetic (inductive) measuring of the conductivity of liquids. Referring to FIG. 1, electromagnetic (inductive) measuring of the conductivity of liquids is performed by immersing a sensor into the solution. The sensor includes at least two toroidal cores T1 and T2. Core T1 carries an excitation coil L1 and core T2 carries an induction coil L2. The measuring device includes an excitation driving circuit to supply the excitation coil inside the sensor with an AC excitation voltage 1 of a certain amplitude by way of the driver 2 and through a DC-blocking capacitor C1, so that an AC current is induced in the loop 6 through the liquid to measure the resistance of the fluid R. This current is coupled to the induction coil L2 of the second toroidal core T2, and as a result an induced current is generated in the induction coil L2. The measuring unit 8 induces the AC induction current or voltage in the induction coil L2.

Next, the conductivity of the liquid is computed by the central processing unit 9. At the end, the final result for the conductivity of the liquid is shown on the display 10, or available at the 4-20 mA output, or sent to an alarm device.

Figure 2:
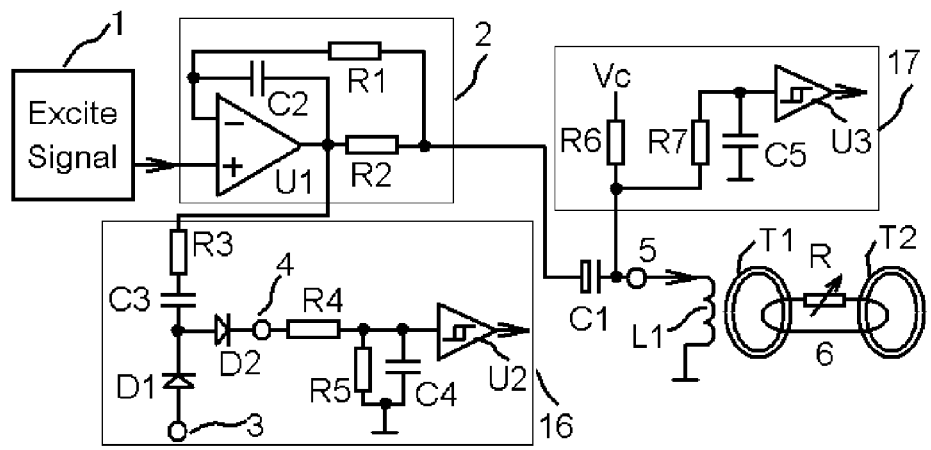
FIG. 2 is a schematic illustrating the principle of an implementation of an exemplary method for inductive measuring of the conductivity of a liquid described herein, which uses the exemplary method according to the invention for detecting an open-circuit failure combined with the exemplary method for detecting a short-circuit failure of the excitation coil.

Referring to FIG. 2, block 2 represents an implementation of the excitation driving circuit presented in FIG. 1; U1 is an operational amplifier which is used as a voltage follower; C2 is a small value capacitor which makes the circuit stable; R1 is a negative feedback resistor; R2 is a current-limiting resistor and also serves for the short-circuit failure detecting circuit of the excitation coil; and block 16 represents the short-circuit failure detecting circuit of the excitation coil. When short-circuit failure occurs at the excitation side, the output swing of excitation driving circuit 2 will be much lower than its normal value. The operational amplifier U1 is connected as a voltage follower, which always tends to normalize the output swing of the excitation driving circuit 2. Because of the existence of the current-limiting resistor R2, the output swing of the operational amplifier U1 will always be as close as possible to the positive or negative supply power levels, which means that the output swing of the operational amplifier U1 in the excitation driving circuit will be much larger than the normal value. Under normal conditions, for example assuming that the excitation voltage of the excitation coil is below or equal to +/−1V, the output swing of the excitation driving circuit 2 is less than or equal to 2V, (for example 2V/0V, +1V/−1V, etc). If R2 is at its proper value, for example 240 ohms, the swing of U1 under normal conditions is a little more than the output swing of the excitation driving circuit 2, for example between +2.3V/−0.3V, or +1.3V/−1.3V. However, if a short-circuit failure occurs at the excitation side, the output swing of U1 will be close to the positive and negative power voltages, for example, +3.1V/−3.1V. R3 and C3 are used to detect the output swing of U1.

R3 and C3 serve for current limiting and DC-blocking, D1 and D2 form a peak-to-peak measuring circuit which generates a voltage for detection, corresponding to the voltage swing of the operational amplifier U1 and outputs at node 4. In this circuit, there is a first diode D1 connected in reverse orientation between the output 3 of the pick-up circuit and the reference voltage, and a second diode connected in forward orientation between the output of the pick-up circuit and the output node 4.

R4, R5 and C4 also form a low-pass filter. R4 and R5 form a voltage-dividing circuit which makes the input more appropriate for the voltage detector U2. The latter is a voltage level detector which can be a gate circuit. Preferably, it is a device like a Schmitt trigger, such as two 74HC14 gates connected in series. If the detected DC voltage exceeds a certain threshold voltage and U2 is activated, this can be judged to be an indication for a short-circuit failure of the excitation coil.

Terminal 3 defines the reference potential of a peak-to-peak detector (D1, D2). It can be connected to ground or preferably to a negative potential such as −1.5V in order to optimize the reliability and to simplify the value selection for R3, R4, R5, C3 and C4. By selecting the values for R3, R4, R5, C3 and C4, the threshold voltage of U2 can be placed so that the normal output swing of the operational amplifier U1 can be distinguished from a short-circuit failure at the excitation side.

In addition, because when a short-circuit failure occurs, the output swing of the excitation driving circuit 2 will be much less than its normal value, the failure can also be detected by directly monitoring the output swing of the excitation driving circuit 2. But in some cases, the specified normal swing is relatively small, such as +0.2V/−0.2V, and the detecting circuit would therefore be somewhat more complicated.

In FIG. 2, block 17 represents the circuit for detecting the open-circuit failure at the excitation side. A very small DC current is supplied by a DC power supply Vc with a large value resistor R6 on the side of the excitation coil L1. Under normal conditions, because the DC resistance of the excitation coil L1 is very small, the DC voltage of terminal 5 is almost zero. Because the excitation DC current is very small, such as several micro amperes, which would never bring the coil into saturation, the accuracy of the measurement is not affected. If an open-circuit failure occurs on the excitation coil L1 or cable, a DC voltage of about the same magnitude as Vc will be generated on terminal 5, which by way of the low pass filter made up of R7 and C5 activates the voltage level detector circuit U3. In order to eliminate the influence of the AC excitation voltage on the voltage level detecting circuit U3, an RC filter (R7, C5) is arranged between the terminal 5 and the level detector circuit U3. The circuit U3 can be a gate circuit. Preferably, it is a device like a Schmitt trigger, for example two 74HC14 gates in series. A low voltage (lower than a certain threshold level) at the input of U3 means that the induction coil and the cable are working normally; conversely, a high voltage at the input of U3 means that there is an open-circuit failure on the side of the exitation coil L1. Thus, the output of U3 can reliably indicate the presence of an open-circuit failure on the excitation coil side.

Figure 3:
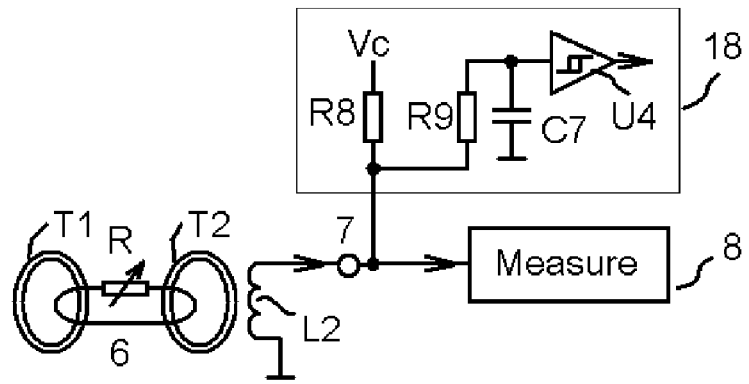
FIG. 3 is a schematic illustrating the principle of an implementation of an exemplary method for inductive measuring of the conductivity of a liquid as described herein, which applies an exemplary method according to the invention for detecting open-circuit failure of the induction coil.

In FIG. 3, block 18 represents one kind of the circuits that can be used for detecting the open-circuit failure on the side of the induction coil L2. In this implementation, the detecting circuit for open-circuit failure of the induction coil is similar to block 17 in FIG. 2. A very small DC current is supplied by a DC power source Vc with a large value resistor R8 on the side of the induction coil L2. Under normal conditions, because the DC resistance of the coil L2 is very small, the DC voltage at terminal 7 is almost zero. If an open-circuit failure occurs in the induction coil L2 or the cable, a DC voltage approximately equal to Vc will be present at the terminal 7. By way of the low pass filter made up of R9 and C7, this DC voltage activates the voltage level detector circuit U4. In order to eliminate the influence of the AC induction voltage on the voltage level detecting circuit U4, an RC filter (R9, C7) is arranged between the terminal 7 and the level detector circuit U4. The circuit U4 can be a gate circuit. Preferably, it is a device like a Schmitt trigger, for example two 74HC14 gates in series. Low voltage (lower than a certain threshold level) at the input of U4 means that the induction coil and the cable are working normally; conversely, a high voltage at the input of U4 means that an open-circuit failure is present on the side of the induction coil L2. Thus, the output of U4 can reliably indicate the presence of an open-circuit failure on the induction coil side.

In addition, the double-toroidal sensor and the measuring device could be connected through a cable as mentioned above. Because the conductivity of the liquid is normally related to its temperature, a temperature sensor (PT100, PT1000 or NTC) is usually included in the liquid conductivity sensor. Thus, there could be additional wires inside the cables connecting the sensor and the measuring device. In addition, there could be temperature-measuring circuits arranged inside the measuring device, and the temperature correction could be calculated by the CPU; there could be devices against magnetic flux leakage and against build-up of electrostatic charges arranged inside the sensor. Certain parameters can be calibrated for the entire system. The general principles for these methods and devices are also applicable to the method and device of the present invention.

The terms, symbols, expressions and examples used in the description above are not in any way meant to limit the scope of the invention, but serve only to illustrate certain aspects of the invention.

The embodiments described above only represent preferred embodiments of the present invention. Various equivalent substitutions and modifications can be made by one skilled in the art based on the foregoing description. Nevertheless, all these substitutions and modifications fall within the spirit of the invention and the scope as defined in the following claims:

What is claimed is:

1. A method for detecting a failure of a measurement device for inductively measuring the electrical conductivity of a fluid medium with a sensor having at least two toroidal cores, wherein a first toroidal core carries an excitation coil and a second toroidal core carries an induction coil, the sensor is connected to a measuring device having an excitation driving circuit to supply an AC excitation voltage to the excitation coil inside the sensor so that a current or voltage, related to the conductivity of the measured liquid, is induced in the induction coil, said method comprising:

applying an additional signal to terminals of at least one of the excitation coil and the induction coil, resulting in a derived signal from the coil having the additional signal;

monitoring the derived signal to detect an open-circuit failure of the device; and monitoring an output swing of the excitation driving circuit in order to detect a short-circuit failure of the device.

2. The method of claim 1, wherein the additional signal is a direct current.

3. The method of claim 2, wherein the strength of the additional signal is insufficient to bring the at least one coil into saturation.

4. The method of claim 1, wherein the derived signal is a voltage.

5. The method of claim 1, further comprising detecting a failure of a measurement device, wherein the failure of the measuring device is selected from the group consisting of: open-circuit failure or short circuit-failure of the sensor, the coil having the additional signal, of a connecting cable connected to the coil having the additional signal, and of a measurement circuit connected to the coil having the additional signal.

6. The method of claim 1, further comprising providing a power source to deliver the additional signal to the excitation coil via a high resistance resistor.

7. The method of claim 1, further comprising:

using an excitation coil to apply an alternating current to the fluid medium;

measuring the output swing of the excitation current to obtain a measurement value;

comparing the measurement value to at least one threshold value; and triggering an action of the measurement device if the measurement value exceeds the at least one threshold value.

8. A circuit for detecting a failure of a device for inductively measuring the electrical conductivity of a fluid medium with a sensor, the sensor comprises at least one excitation coil or induction coil, for applying to the fluid medium or receiving from the fluid medium an alternating current, said detection circuit comprising:

a means for applying a DC signal to at least one of the excitation coil and the induction coil, to generate a derived signal from the coil having the DC signal, wherein the derived signal is monitored in order to detect an open-circuit or a short circuit failure of the measurement device;

a measurement unit connected to the coil having the DC signal to measure the derived signal for obtaining a measurement value;

a level detector connected to the measurement unit, said level detector configured to compare the measurement value to at least one threshold value to obtain a comparing result; and an output to trigger an action of the measurement device if the measured value exceeds the at least one threshold value, wherein the means for applying the DC signal is a DC power source connected to the coil having the DC signal by a high resistance resistor.

9. The detection circuit of claim 8, wherein the power source applies a substantially continuous signal to the coil having the DC signal.

10. The detection circuit of claim 8, wherein the level detector is connected to a display unit.

11. The detection circuit of claim 8, wherein the level detector is connected to a processing device to transmit the comparing result for triggering the action of the measurement device.

12. The measurement device of claim 11, comprising:
a inductive conductivity sensor operably connected to the measurement unit, wherein the sensor is immersed into the fluid medium.

13. The measurement device of claim 12, wherein said at least one excitation coil or induction coil is carried by a toroidal core.

14. A measurement device, comprising:
a detection circuit according to claim 8; and
an excitation driving circuit, said excitation driving circuit including:
an operation amplifier, said operational amplifier having a positive output connected to an excitation signal;
a negative feedback resistor, said negative feedback resistor connecting a negative input of the operational amplifier and the output of the excitation driving circuit also connected to the at least one excitation coil; and
a current-limiting resistor, said current-limiting resistor connecting the excitation driving circuit and the at least one excitation coil.

15. The measurement device of claim 14, further comprising a second detecting circuit for detecting a short-circuit failure of the excitation driving circuit, said second detecting circuit comprising:
a pick-up circuit connected to the output of the operational amplifier;
a peak-to-peak measuring circuit connected to an output of the pick-up circuit, said peak-to-peak measuring circuit generates a voltage representing a voltage swing of the operational amplifier, said voltage is available for detection; and
a voltage level detector connected to said voltage, said voltage level detector operable to diagnose a short-circuit failure on the at least one excitation coil if the voltage exceeds a threshold voltage.

16. The measurement device of claim 15, wherein the peak-to-peak measuring circuit includes:
a first diode connected in reverse orientation between an output of the pick-up-circuit and a reference voltage source;
a second diode connected in forward orientation between the output of the pick-up circuit and an output node, said output node outputs the voltage that is available for detection; and
a voltage dividing circuit interposed between the output node and the voltage level detector.

* * * * *